United States Patent
Kim et al.

(10) Patent No.: US 11,302,094 B2
(45) Date of Patent: Apr. 12, 2022

(54) SYSTEM AND METHOD FOR SEGMENTING NORMAL ORGAN AND/OR TUMOR STRUCTURE BASED ON ARTIFICIAL INTELLIGENCE FOR RADIATION TREATMENT PLANNING

(71) Applicants: SAMSUNG LIFE PUBLIC WELFARE FOUNDATION, Seoul (KR); SEOUL NATIONAL UNIVERSITY R&DB FOUNDATION, Seoul (KR)

(72) Inventors: Heejung Kim, Seoul (KR); Ji Min Lee, Daejeon (KR); Hyung Joo Cho, Seoul (KR); Sung Joon Ye, Seoul (KR)

(73) Assignees: SAMSUNG LIFE PUBLIC WELFARE FOUNDATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 168 days.

(21) Appl. No.: 16/946,480

(22) Filed: Jun. 24, 2020

(65) Prior Publication Data
US 2021/0103756 A1     Apr. 8, 2021

(30) Foreign Application Priority Data
Oct. 8, 2019     (KR) .......................... 10-2019-0124823

(51) Int. Cl.
*G06K 9/00*     (2022.01)
*G06V 10/44*     (2022.01)
(Continued)

(52) U.S. Cl.
CPC ........... *G06V 10/44* (2022.01); *A61N 5/1039* (2013.01); *G06K 9/6256* (2013.01);
(Continued)

(58) Field of Classification Search
CPC . B01J 2/16; B01J 8/245; B05B 13/025; Y10S 118/05; A61N 5/1031;
(Continued)

(56) References Cited

U.S. PATENT DOCUMENTS

| | | | | |
|---|---|---|---|---|
| 2014/0003695 A1* | 1/2014 | Dean | ....................... | G06T 17/00 382/131 |
| 2015/0065859 A1* | 3/2015 | Hwang | ................... | G06T 7/143 600/411 |

(Continued)

FOREIGN PATENT DOCUMENTS

| | | |
|---|---|---|
| KR | 10-0952817 B1 | 4/2010 |
| KR | 10-2012-0007862 A | 1/2012 |

(Continued)

OTHER PUBLICATIONS

Lee et al. "Deep-learning-based label-free segmentation of cell nuclei in time-lapse refractive index tomograms" IEEE, 18 pp (Nov. 2018).

(Continued)

*Primary Examiner* — Xin Jia
(74) *Attorney, Agent, or Firm* — Myers Bigel, P.A.

(57) ABSTRACT

The present disclosure relates to a system and method for segmenting a normal organ and/or tumor structure based on artificial intelligence for radiation treatment planning. The system may include a data collection unit configured to collect a radiotherapy structure (RT-structure) file including a computerized tomography (CT) image of a patient and contour information of an area of interest for radiation treatment, a pre-processing unit configured to extract the contour information from the RT-structure file and generate a binary image based on the extracted contour information, and a model training unit configured to learn parameters for generating a segmentation map indicative of the area of interest using a deep learning algorithm, based on the binary (Continued)

image, and generate a trained model based on the learnt parameter.

12 Claims, 10 Drawing Sheets

(51) Int. Cl.
　　　G16H 50/20　　　(2018.01)
　　　G16H 20/40　　　(2018.01)
　　　G16H 30/20　　　(2018.01)
　　　G16H 30/40　　　(2018.01)
　　　G06N 3/04　　　　(2006.01)
　　　G06K 9/62　　　　(2022.01)
　　　A61N 5/10　　　　(2006.01)
　　　G06N 3/08　　　　(2006.01)

(52) U.S. Cl.
　　　CPC ............ *G06K 9/6262* (2013.01); *G06N 3/04* (2013.01); *G06N 3/08* (2013.01); *G16H 20/40* (2018.01); *G16H 30/20* (2018.01); *G16H 30/40* (2018.01); *G16H 50/20* (2018.01); *G06V 2201/031* (2022.01)

(58) Field of Classification Search
　　　CPC ........... A61N 5/1039; G06K 2209/051; G06K 9/4604; G06K 9/6256; G06K 9/6262; G06K 9/6271; G06N 3/04; G06N 3/0454; G06N 3/08; G16H 20/40; G16H 30/20; G16H 30/40; G16H 50/20
　　　See application file for complete search history.

(56) References Cited

U.S. PATENT DOCUMENTS

2018/0259608 A1*　9/2018　Golden .................... G06T 7/11
2019/0239926 A1*　8/2019　Pavlovskaia ........... A61B 90/37
2019/0388123 A1*　12/2019　Pavlovskaia ........... G16H 50/50

FOREIGN PATENT DOCUMENTS

KR　　10-1760287 B1　　7/2017
KR　　10-1857624 B1　　5/2018

OTHER PUBLICATIONS

Lee et al. "Deep-learning-based label-free segmentation of cell nuclei in time-lapse refractive index tomograms" IEEE, vol. 7, 12 pp (Jun. 2019).

* cited by examiner

SYSTEM AND METHOD FOR SEGMENTING NORMAL ORGAN AND/OR TUMOR STRUCTURE BASED ON ARTIFICIAL INTELLIGENCE FOR RADIATION TREATMENT PLANNING

CROSS-REFERENCE TO RELATED APPLICATION

This U.S. non-provisional patent application claims priority under 35 U.S.C. § 119 to Korean Patent Application No. 10-2019-0124823, filed on Oct. 8, 2019, in the Korean Intellectual Property Office, the disclosure of which is hereby incorporated by reference in its entirety.

BACKGROUND

1. Technical Field

The present disclosure relates to a system and method for segmenting a normal organ and/or tumor structure based on artificial intelligence for radiation treatment planning, in particular, to a system and method for automating a task for segmenting a normal organ and/or tumor structure, which is necessary when working out a radiation treatment plan, using high-dimensional features optimized and extracted through learning from an artificial intelligence model.

2. Related Art

In general, in order to reduce side effects attributable to radiation exposure and increase the accuracy of treatment, a process of working out a radiation treatment plan is performed prior to substantial radiation treatment for a patient. For example, in the process of working out a radiation treatment plan, a task for selecting a normal organ and/or tumor portion, that is, a target of radiation treatment, is performed based on images of a treatment area of a patient.

The task for selecting a normal organ and/or tumor portion is a task for segmenting an area, that is, a target, from a video or image of a treatment area of a patient. The task is chiefly performed by a clinician's empirical judgment. The task for selecting a normal organ and/or tumor portion is inevitably influenced by a degree of mastery of a clinician and a substantial amount of time must be taken to complete the task because it is not easy to prepare a given rule or criterion itself.

Organ segmentation researches based on previous treatment plan data are actively carried out for a speed increase and automation in working out a radiation treatment plan, but conventional researches chiefly use a method of segmenting a normal organ and/or tumor portion, the target, from a video or image based on a rule regulated by human. The accuracy of conventional researches is significantly low compared to the existing task performed by a clinician's empirical judgment because it is not easy to prepare a given rule or criterion for selecting a normal organ and/or tumor portion as described above.

PRIOR ART DOCUMENT

[Patent Document]
Korean Patent Application Publication No. 10-2015-0094080 (Aug. 19, 2015)

SUMMARY

Various embodiments are directed to the provision of a system and method for optimizing an automated process of segmenting an area of interest on a computerized tomography (CT) image of a patient by segmenting the area of interest using high-dimensional features, trained through a deep learning algorithm, not a given rule or a human's empirical judgment, in working out a radiation treatment plan.

In an embodiment, a system for segmenting a normal organ and/or tumor structure based on artificial intelligence for radiation treatment planning may include a data collection unit configured to collect a radiotherapy structure (RT-structure) file including a computerized tomography (CT) image of a patient and contour information of an area of interest for radiation treatment, a pre-processing unit configured to extract the contour information from the RT-structure file and generate a binary image based on the extracted contour information, and a model training unit configured to learn parameters for generating a segmentation map indicative of the area of interest using a deep learning algorithm, based on the binary image, and generate a trained model based on the trained parameters.

In an embodiment, the contour information may be information on the locations of points forming the contour of the area of interest. The pre-processing unit may be configured to generate a polygonal contour line based on the information on the locations of the points and to generate the binary image by assigning a binary value based on whether the points are located inside or outside the polygonal contour line.

In an embodiment, the model training unit may be configured to use a data augmentation algorithm in order to increase the amount of data for training.

In an embodiment, the model training unit may be configured to classify the CT images and the binary images into training data or validation evaluation data and to verify the plural trained models by inputting the validation data into the trained models based on the training data.

In an embodiment, the system may further include a inference unit configured to generate a segmentation map for a plurality of CT images using the trained model when the CT images are input through the data collection unit and a data conversion unit configured to convert the segmentation map, generated by the data inference unit, into an RT-structure file and transmit the converted RT-structure file to a radiation treatment planning system.

In an embodiment, the data inference unit may be configured to estimate the area of interest for the plurality of CT images at intervals of N (N is a natural number) data using the trained model and to perform interpolation for the estimation of an approximate value on the remaining CT images for which an area of interest has not been estimated.

In an embodiment, the data inference unit may be configured to perform corrections on a misjudgment for an area of interest configuring the segmentation map, the size of the area of interest or a contour line of the area of interest.

In an embodiment, the data inference unit may be configured to remove an area of interest having a given size or less of an area, determined to be the area of interest although the area is not the area of interest, from the segmentation map, smooth a contour line of the segmentation map, compare the sizes of segmentation maps of adjacent CT images, and perform interpolation based on the result of the comparison.

In an embodiment, a method of segmenting a normal organ and/or tumor structure based on artificial intelligence for radiation treatment planning may include collecting, by a data collection unit, a radiotherapy structure (RT-structure) file including a computerized tomography (CT) image of a patient and contour information of an area of interest for radiation treatment, extracting, by a pre-processing unit, the contour information from the RT-structure file and generating a binary image based on the extracted contour information, learning, by a model training unit, parameters for generating a segmentation map for a given CT image using a deep learning algorithm, based on the binary image, and generating, by the model training unit, a trained model based on the trained parameters.

In an embodiment, the contour information may be information on the locations of points forming the contour of the area of interest. The generating of the binary image may include generating, by the pre-processing unit, a polygonal contour line based on the information on the locations of the points and generating the binary image by assigning a binary value based on whether the points are located inside or outside the polygonal contour line.

In an embodiment, the generating of the trained model may include classifying the CT images and the binary images into training data or validation data and verifying the plural trained models by inputting the validation data into the trained models based on the learnt data.

In an embodiment, the method may further include generating, by a data inference unit, a segmentation map for a plurality of CT images using the trained model when the CT images are input through the data collection unit and converting, by a data conversion unit, the segmentation map, generated by the data inference unit, into an RT-structure file, and transmitting the converted RT-structure file to a radiation treatment planning system.

In an embodiment, the generating of the segmentation map may include removing an area of interest having a given size or less of an area, determined to be the area of interest although the area is not the area of interest, from the segmentation map, smoothing a contour line of the segmentation map, and comparing the sizes of segmentation maps of adjacent CT images and performing interpolation based on a result of the comparison.

In an embodiment, there may be provided a computer-readable recording medium in which a program for executing the above-described method in a computer has been written.

DETAILED DESCRIPTION

Terms used in this specification are briefly described, and embodiments of the present disclosure are then described in detail.

Terms used in the present disclosure are common terms which are now widely used by taking into consideration functions in the present disclosure, but the terms may be changed depending on an intention of those skilled in the art, a precedent, or the advent of a new technology. Furthermore, in a specific case, some terms are randomly selected by the applicant. In this case, the meaning of a corresponding term is described in detail in a corresponding part of the detailed description. Accordingly, terms used in this specification should not be defined simply based on their names, but should be defined based on their substantial meanings and contents over this specification.

In the entire specification, unless explicitly described to the contrary, the word "include" and variations, such as "includes" or "including", will be understood to imply the inclusion of stated elements but not the exclusion of any other elements. Furthermore, the term " . . . unit" or "module" described in the specification means a unit for processing at least one function or operation, and the unit may be implemented by hardware or software or a combination of hardware and software.

Embodiments of the present disclosure are described hereinafter in detail with reference to the accompanying drawings, in order for a person having ordinary skill in the art to which the present disclosure pertains to carry out the present disclosure. The present disclosure may be modified in various different ways, and is not limited to the disclosed embodiments herein. In order to clarify a description of the disclosure, a description of parts not related to the description is omitted, and the same reference numbers are used throughout the specification to refer to the same or like parts.

Hereinafter, various examples of embodiments will be described in detail with reference to the accompanying drawings.

Figure 1:
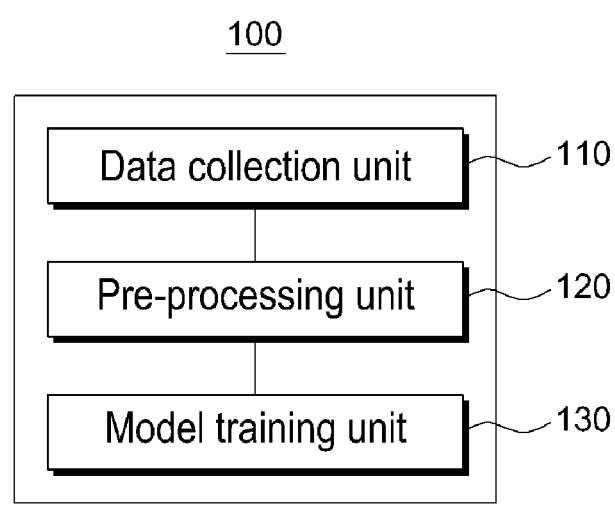
FIG. 1 is a block diagram illustrating a system for segmenting a normal organ and/or tumor structure based on artificial intelligence for radiation treatment planning according to a first embodiment of the present disclosure.
Figure 2:
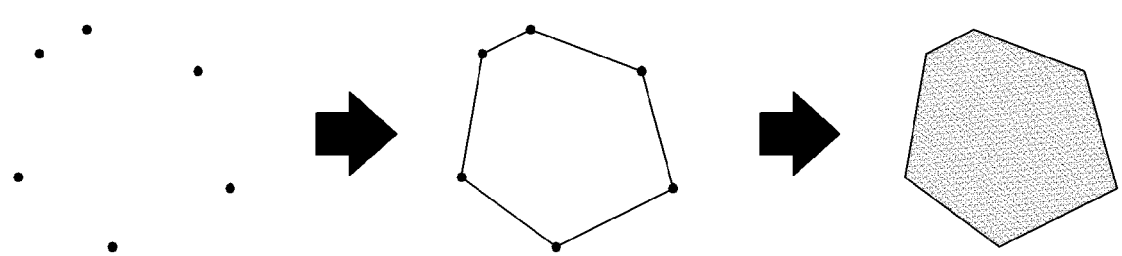
FIG. 2 is a concept view illustrating a pre-processing step for training a deep learning model according to an embodiment of the present disclosure.

FIG. 1 is a block diagram illustrating a system 100 for segmenting a normal organ and/or tumor structure based on artificial intelligence for radiation treatment planning according to a first embodiment of the present disclosure. FIG. 2 is a concept view illustrating a pre-processing step for training a deep learning model according to an embodiment of the present disclosure.

Figure 3:
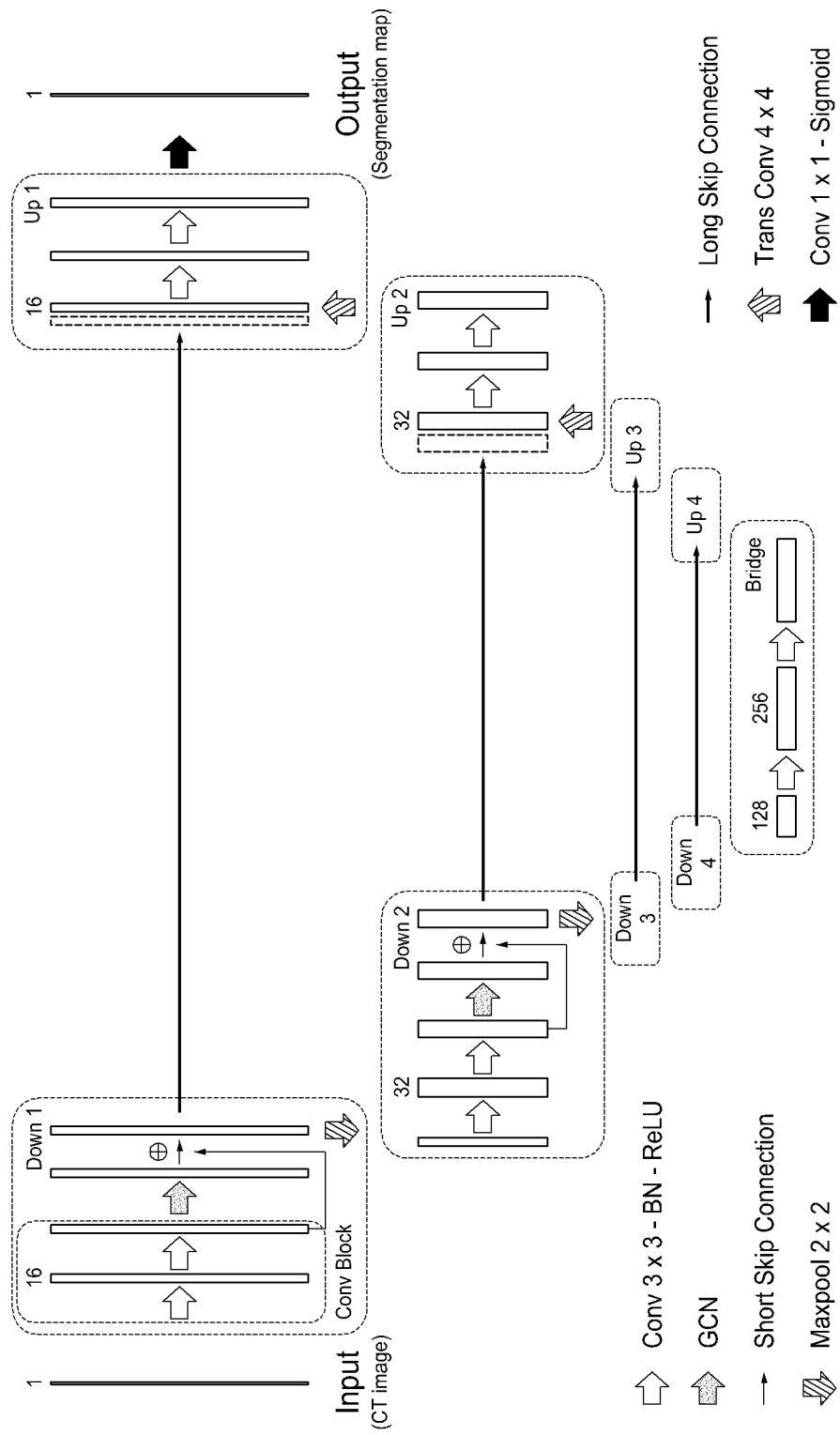
FIG. 3 is a structural diagram illustrating a deep learning model according to an embodiment of the present disclosure.
Figure 4:
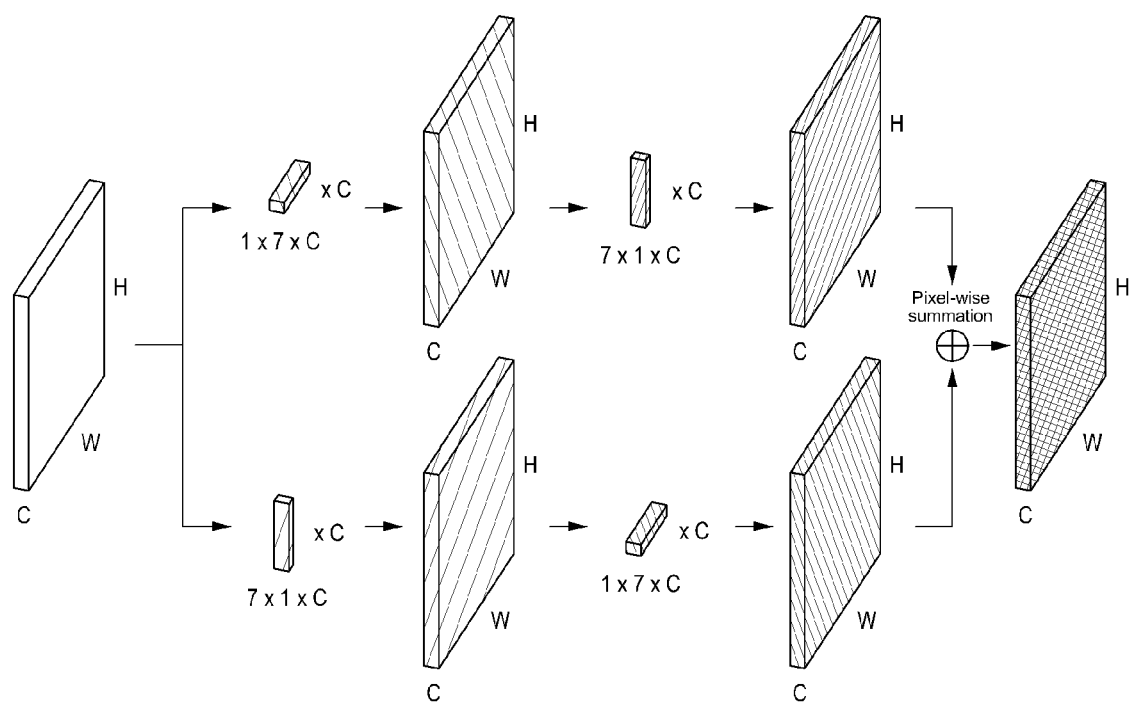
FIG. 4 is a structural diagram illustrating a global convolutional network (GCN) algorithm according to an embodiment of the present disclosure.

Furthermore, FIG. 3 is a structural diagram illustrating a deep learning model according to an embodiment of the present disclosure. FIG. 4 is a structural diagram illustrating a global convolutional network (GCN) algorithm according to an embodiment of the present disclosure.

Referring to FIG. 1, the system 100 for segmenting a normal organ and/or tumor structure based on artificial intelligence for radiation treatment planning according to the first embodiment of the present disclosure may include a data collection unit 110 configured to collect a radiotherapy structure (RT-structure) file including a computerized tomography (CT) image of a patient and contour information of an area of interest for radiation treatment, a pre-processing unit 120 configured to extract the contour information from the RT-structure file and generate a binary image based on the extracted contour information, and a model training unit 130 configured to learn parameters for generating a segmentation map indicative of the area of interest using a deep learning algorithm, based on the binary image, and generate a trained model based on the trained parameters.

A CT image according to an embodiment of the present disclosure is basic data necessary for the learning and inference process of the system 100 for working out a radiation treatment plan, and refers to data stored in a digital imaging and communications in medicine (DICOM) format. For example, information on a CT image may be included in a lower category of a header called "Pixel Data" within a DICOM file. Accordingly, the data collection unit 110 may collect a DICOM file and obtain a CT image by loading the lower category of the collected DICOM file.

An RT-structure file according to an embodiment of the present disclosure refers to basic data necessary to obtain contour information of major organs (i.e., organs of interest, that is, a target of radiation treatment) to be segmented in order to work out a radiation treatment plan. In this case, the contour information refers to information on the contour line of an area of interest drawn based on a clinician's judgment for radiation treatment. That is, the system 100 according to an embodiment of the present disclosure may use information on the existing contour line of an area of interest drawn based on a clinician's empirical judgment, in order to learn the area of interest for radiation treatment in a patient's CT image.

The pre-processing unit 120 according to an embodiment of the present disclosure may extract contour information from an RT-structure file. In this case, the contour information refers to information on the locations of points forming the contour of an area of interest. For example, the RT-structure file may be stored in a DICOM format like a CT image. The pre-processing unit 120 may extract contour information of an area of interest, included in a lower category of a header called "ROI Contour Sequence" within an RT-structure file, for each slice. In this case, the contour information for each slice has been stored as a combination of points represented as X, Y and Z coordinate values.

Referring to FIG. 2, the pre-processing unit 120 according to an embodiment of the present disclosure may generate a polygonal contour line based on contour information, and may generate a binary image by assigning a binary value based on whether points configuring the contour are located inside or outside the polygonal contour line. For example, when contour information corresponding to information on the locations of six points is extracted from an RT-structure file as illustrated in FIG. 2, the pre-processing unit 120 may generate a hexagonal contour line using the information on the locations of the six points. When the hexagonal contour line is generated, the pre-processing unit 120 may convert the contour information into a binary image by assigning a value of 1 to a point located inside the polygonal contour line and a value of 0 to a point located outside the polygonal contour line.

The model training unit 130 according to an embodiment of the present disclosure may learn parameters of a trained model by which an area of interest in a patient's CT image is segmented most closely to a binary image. For example, the model training unit 130 may learn parameters using a binary cross entropy (BCE) loss function in order to minimize a difference between a CT image, that is, an input value, and a binary image corresponding to a correct answer value. Furthermore, the model training unit 130 may use an ADAM optimizer in which both a learning rate indicating how much learning will be performed at once and a gradient indicating which direction learning will be performed in are taken into consideration, in order to improve the speed of updating model's parameters.

The model training unit 130 according to an embodiment of the present disclosure may use a data augmentation algorithm in order to increase the amount of data for updating parameters. The data augmentation algorithm is used to improve performance of a convolutional neural network (CNN) and is a method of changing a pixel without changing the label of an image. For example, the model training unit 130 may perform an augmentation algorithm, such as a horizontal flip, rotation or a random crop, on one binary image. The number of binary images itself used for updating parameters can be increased because images on which the augmentation is performed are recognized as different data. The number of binary images augmented as described above may be adjusted by a user according to the progress of training a model.

A data augmentation algorithm according to an embodiment of the present disclosure may include an elastic deformation algorithm for deforming the structure of an image pixel. Unlike a data augmentation algorithm, such as a horizontal flip, rotation or a random crop, the elastic deformation algorithm is a method of randomly deforming an outward appearance of each of pixels configuring an image. Such an elastic deformation algorithm is an augmentation method suitable for medical data compared to other data augmentation algorithms, such as the above-described data augmentation algorithm. Accordingly, the model training unit 130 can perform efficient learning having high segmentation accuracy using the elastic deformation algorithm although the amount of data itself collected for training is limited.

The model training unit 130 according to an embodiment of the present disclosure may generate a trained model using parameters learnt through the above-described process. For example, the trained model may be configured like FIG. 3. Referring to FIG. 3, the trained model may have unique elements, such as a short skip connection (SSC), based on a global convolutional network (GCN) and an encoder-decoder structure. The trained model may be divided into a feature extraction step (i.e., encoder part) and a spatial resolution recovery step (i.e., decoder part). In this case, the feature extraction step includes a total of four down modules, and the spatial resolution recovery step includes a total of four up modules. The number of down modules and the number of up modules may be changed suitably for data characteristics.

Referring to FIG. 3, one down module may have a convolution block including two sets of convolution layers having a 3×3 filter, and may perform an activation function through batch normalization and an active function (e.g., rectified linear unit (ReLU)). A global convolutional network (GCN) layer subsequent to the convolution block may extract features having different features along an axis. Furthermore, a feature map subsequent to the GCN layer may be combined with a feature map prior to the GCN layer. Such a process is called a short skip connection (SSC). The size of the feature map can be reduced by half (i.e., from N×N to N/2×N/2) because a 2×2 maxpooling layer is located at the last part of the down module.

Referring to FIG. 3, a bridge portion having only one convolution block is present after the four down modules, and may be connected to the four up modules. The size of a feature map can be increased (i.e., from N×N to 2N×2N) because one up module includes an up convolution (or transposed convolution) layer having a 4×4 filter. The up-sampled feature map may be connected to a feature map having the same level as the up module. This is a long skip connection (LSC) for transmitting spatial information in all levels. After a conversion block performs an LSC again, the final segmentation map may be output through a 1×1 convolution and sigmoid function after the four up modules. The structure of such a trained model (i.e., such as FIG. 3) is only an example, and the architecture of deep learning model of the present disclosure may be configured with several deformable convolution neural network structures, including the above-described example.

FIG. 4 is a structural diagram illustrating a global convolutional network (GCN) algorithm according to an embodiment of the present disclosure.

The GCN algorithm is an operation process for extracting more various and deep features along with features extracted in the existing convolution operation. Referring to FIG. 4, in the GCN algorithm, 1×N and N×1 (e.g., N=7) filters may extract features by performing respective operations on one input at the same time, and may then perform N×1 and 1×N operations. The extraction of high-dimensional features may be completed through an operation (i.e., summation) in which two feature maps extracted through such a process are merged in a pixel unit. The structure of a GCN algorithm, such as FIG. 4, may be positioned between all network structures, and may perform an effective role in extracting more various features along with a convolution operation.

The model training unit 130 according to an embodiment of the present disclosure may perform a task for generating and verifying a plurality of models in a learning process in order to generate an optimal trained model even by using the amount of limited data. For example, the model training unit 130 may classify CT images, collected by the data collection unit 110, and binary images, generated by the pre-processing unit 120, into training data and validation data. In this case, a CT image and binary image separated into the training data are used to learn internal parameters of the deep learning model. Furthermore, the validation data is not used to train of the model (i.e., the update of internal parameters), and is used to evaluate performance of a model trained up to given timing.

That is, the model training unit 130 may generate or update a plurality of trained models using the training data, and may verify the plurality of trained models by inputting validation data to the trained models. If the final performance of each of the models is checked through such verification, the model training unit 130 may determine a trained model having the best performance (i.e., a trained model having the highest accuracy in the segmentation of an area of interest) as the final trained model.

Figure 5:
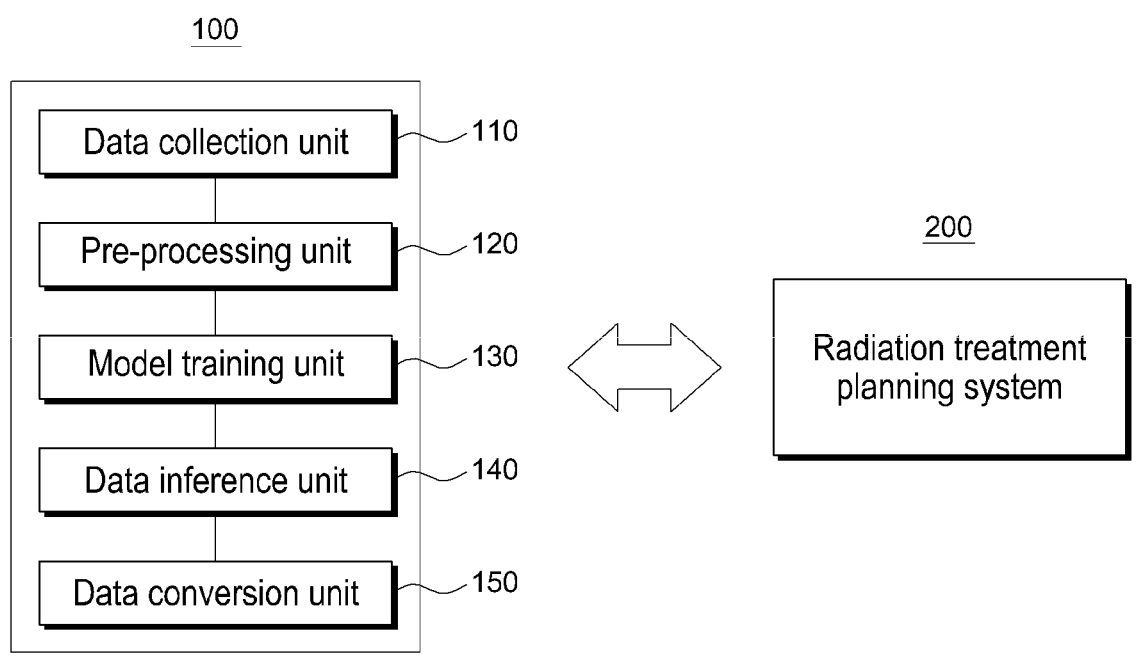
FIG. 5 is a block diagram illustrating a system for segmenting a normal organ and/or tumor structure based on artificial intelligence for radiation treatment planning according to a second embodiment of the present disclosure.

FIG. 5 is a block diagram illustrating a system 100 for segmenting a normal organ and/or tumor structure based on artificial intelligence for radiation treatment planning according to a second embodiment of the present disclosure.

Referring to FIG. 5, the system 100 according to the second embodiment of the present disclosure may further include an inference unit 140 configured to generate a segmentation map for a plurality of CT images using a trained model when the plurality of CT images is input through the data collection unit 110, and a data conversion unit 150 configured to convert the segmentation map, generated by the data inference unit 140, into an RT-structure file and transmit the converted RT-structure file to a radiation treatment planning system 200. The first embodiment of FIG. 1 illustrates a configuration of the system 100 for generating (i.e., training) a trained model. The second embodiment of FIG. 5 illustrates a configuration of the system 100 for automatically segmenting (i.e., inferring) an area of interest.

That is, according to the second embodiment of the present disclosure, when new CT images for working out a radiation treatment plan are input through the data collection unit 110 from an external terminal (e.g., medical database), the data inference unit 140 may generate segmented images for the new CT images using a training model finally determined through the model training unit 130. The data conversion unit 150 may convert the segmented images, generated by the data inference unit 140, into an RT-structure file, and may transmit the converted file to the radiation treatment planning system 200 operating in conjunction with the system 100.

The data inference unit 140 according to an embodiment of the present disclosure may estimate an area of interest for a plurality of CT images at intervals of N (N is a natural number) data using a trained model, and may perform interpolation for the estimation of an approximate value on the remaining CT images for which an area of interest has not been estimated. The interpolation is a statistical prediction method and refers to a method of estimating an unidentified data value using an identified data value.

For example, if a tumor is to be segmented from a total of 30 sheets of CT images and N=2, the data inference unit 140 may perform inference at intervals of two sheets of images (i.e., a total of 15 sheets) and then perform interpolation on the remaining images (i.e., the remaining 15 sheets of the 30 sheets). If N=1, the data inference unit 140 does not perform separate interpolation because a learning model infers all the images. N is a value which may be changed by a user according to use purposes. As N is increased, the processing speed of the data inference unit 140 is improved, but the accuracy of segmentation may be reduced because much interpolation is performed. This is limitedly applied to a two-dimensional deep learning model. If a three-dimensional learning model is used, separate interpolation is not performed in this step.

The data inference unit 140 according to an embodiment of the present disclosure may perform a task for post-processing the image area of a normal organ and/or tumor, that is, a target of radiation treatment, before the results of the segmentation of a CT image are converted into an RT-structure file. Such a post-processing task means that the data inference unit 140 performs corrections on a misjudgment of an area of interest configuring a segmentation map, the size of the area of interest, or the contour line of the area of interest.

For example, the data inference unit 140 may remove an area of interest having a given size or less of an area, determined to be the area of interest although the area is not the area of interest, from a segmentation map generated through a trained model. In this case, the given size may be configured or changed by a user. That is, in the segmentation map, a value of 1 is assigned to an area of interest and a value of 0 is assigned to an area of no interest. Accordingly, the data inference unit 140 may automatically assign a value of 0 to an area having a given size or less in a segmentation map for one CT image. Furthermore, the data inference unit 140 may determine whether a value of 1 has been assigned to an area of no interest, and may modify a value of the corresponding area into a value of 0 if a value of 1 is assigned to the area of no interest.

When the aforementioned primary correction is completed, the data inference unit 140 may smooth the contour line of the segmentation map (preferably, the contour line of an area of interest). Smoothing means a process of generating an approximation function for capturing an important pattern of data by removing noise, the structure of other fine scale, or a sudden change. That is, the data inference unit 140 may perform smoothing for smoothly processing a contour line so that the radiation treatment planning system 200 can smoothly analyze a segmented area of interest. In this case, a correction value for smoothing may be configured or changed by a user.

When the aforementioned secondary correction is completed, the data inference unit 140 may finally compare the sizes of segmentation maps of adjacent CT images, and may perform interpolation based on a result of the comparison. The data inference unit 140 may determine whether the size of an area of interest of a specific slice is a given reference value or less compared to other areas of interest to adjacent slices by comparing the sizes of the areas of interest for each image slice on a given axis (e.g., z axis). If the size of the area of interest of the specific slice is the given reference value or less compared to the areas of interest of the other adjacent slices, the data inference unit 140 may substitute the area of interest of the specific slice with a value of 0, may perform interpolation for estimating the area of interest of the specific slice based on the areas of interest of other slices adjacent to the specific slice. An error of a segmentation map generated by a trained model can be effectively corrected and the accuracy of inference can be improved, through such a three-step correction.

Figure 6:
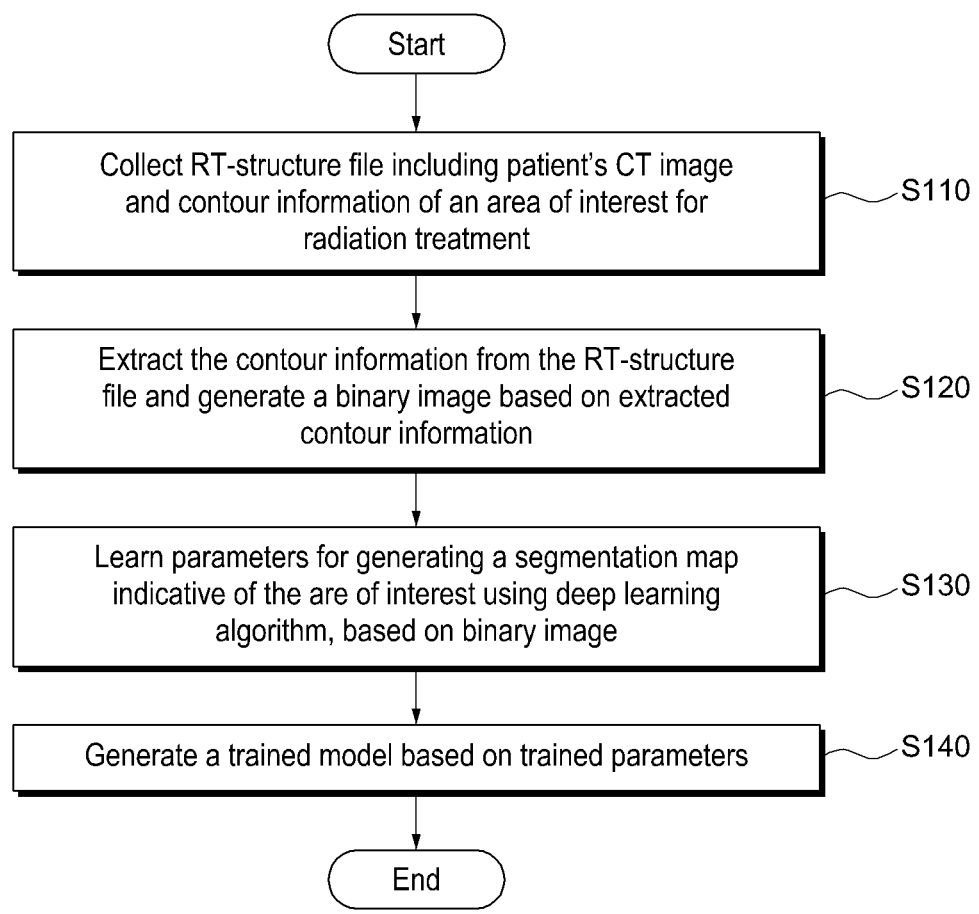
FIG. 6 is a flowchart illustrating a learning process of the system for segmenting a normal organ and/or tumor structure based on artificial intelligence for radiation treatment planning according to an embodiment of the present disclosure.

FIG. 6 is a flowchart illustrating a learning process of the system 100 for segmenting a normal organ and/or tumor structure based on artificial intelligence for radiation treatment planning according to an embodiment of the present disclosure.

Referring to FIG. 6, a method of segmenting a normal organ and/or tumor structure based on artificial intelligence for radiation treatment planning according to an embodiment of the present disclosure may include the step S110 of collecting, by the data collection unit 110, an RT-structure file including a CT image of a patient and contour information of an area of interest for radiation treatment, the step S120 of extracting, by the pre-processing unit 120, the contour information from the RT-structure file and generating a binary image based on the extracted contour information, the step S130 of learning, by the model training unit 130, parameters for generating a segmentation map for a given CT image using a deep learning algorithm, based on the binary image, and the step S140 of generating, by the model training unit 130, a trained model based on the trained parameters.

Figure 7:
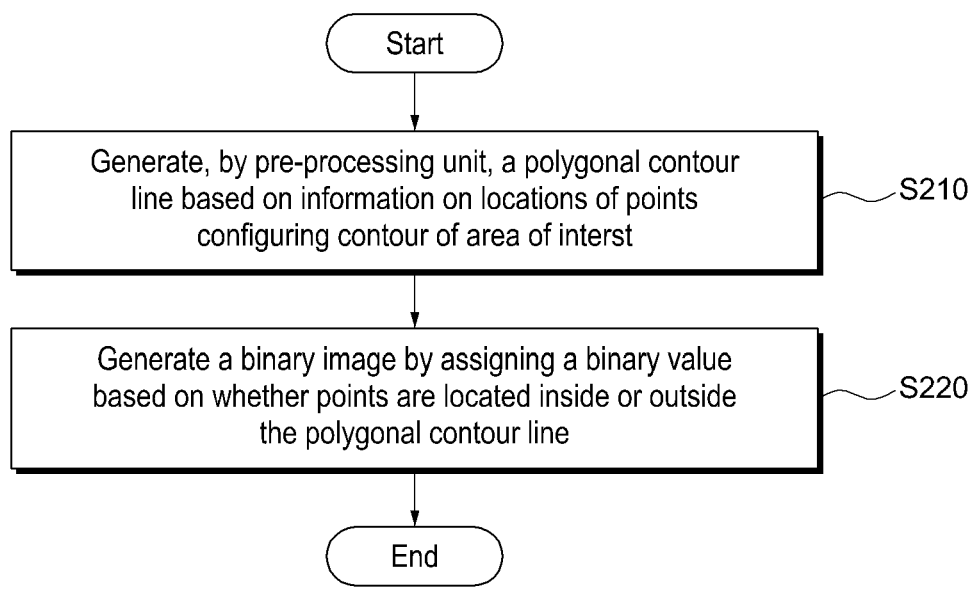
FIG. 7 is a flowchart illustrating a pre-processing step for training a deep learning model according to an embodiment of the present disclosure.

FIG. 7 is a flowchart illustrating a pre-processing step for training a deep learning model according to an embodiment of the present disclosure.

Referring to FIG. 7, the step S120 of generating a binary image according to an embodiment of the present disclosure may include the step S210 of generating, by the pre-processing unit 120, a polygonal contour line based on information on the locations of points and the step S220 of generating a binary image by assigning a binary value based on whether the points are located inside or outside the polygonal contour line.

Figure 8:
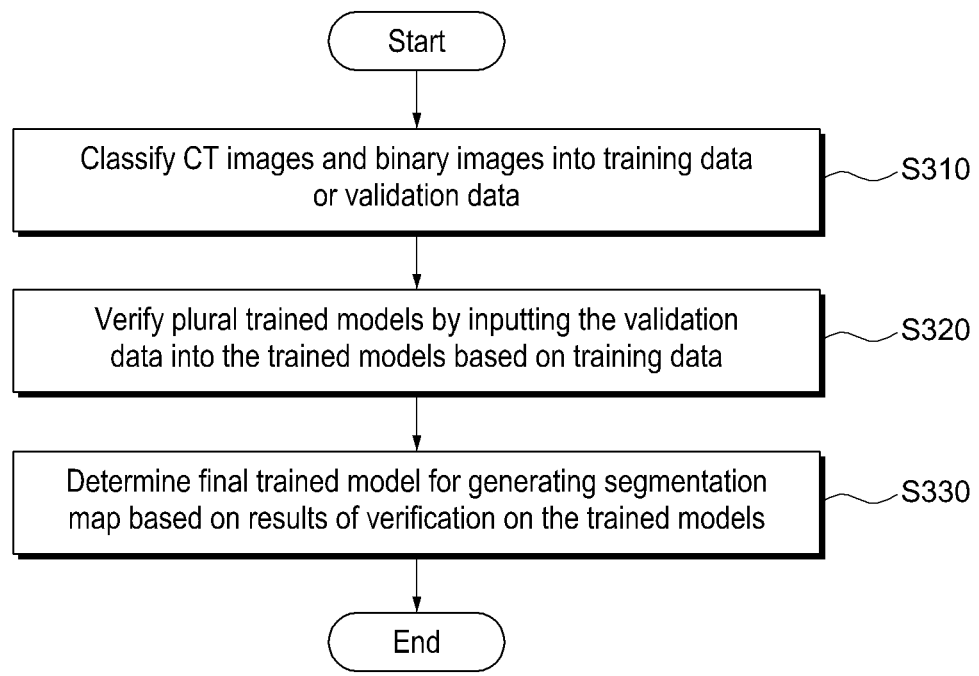
FIG. 8 is a flowchart illustrating a process of finalizing a trained model according to an embodiment of the present disclosure.

FIG. 8 is a flowchart illustrating a process of finalizing a trained model according to an embodiment of the present disclosure.

Referring to FIG. 8, the step S140 of generating a trained model according to an embodiment of the present disclosure may include the step S310 of classifying CT images and binary images into training data or validation data, the step S320 of verifying a plural trained models by inputting validation data into the trained models based on the training data, and the step S330 of determining the final trained model for generating a segmentation map based on the results of the verification on the trained models.

Figure 9:
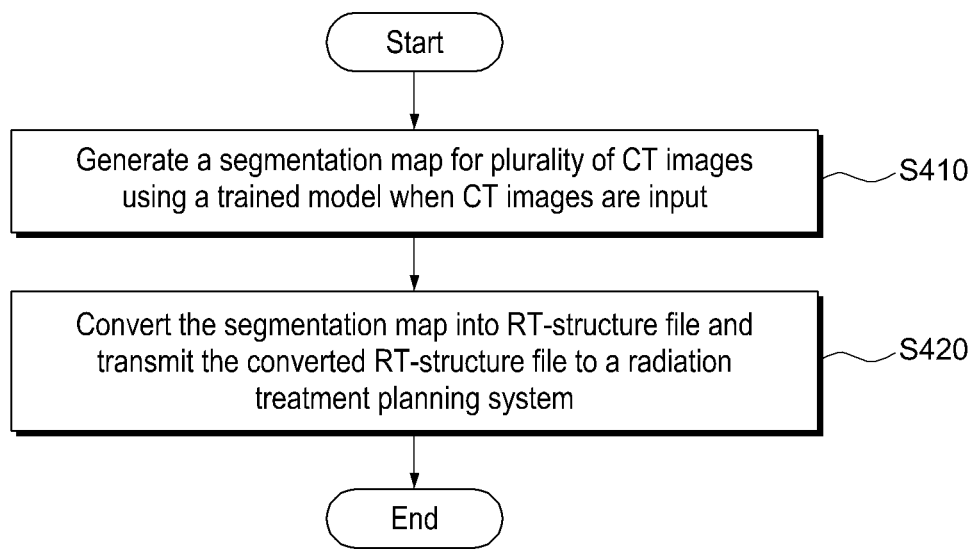
FIG. 9 is a flowchart illustrating an inference process of the system for segmenting a normal organ and/or tumor structure based on artificial intelligence for radiation treatment planning according to an embodiment of the present disclosure.

FIG. 9 is a flowchart illustrating an inference process of the system 100 for segmenting a normal organ and/or tumor structure based on artificial intelligence for radiation treatment planning according to an embodiment of the present disclosure.

Referring to FIG. 9, the method of segmenting a normal organ and/or tumor structure based on artificial intelligence for radiation treatment planning according to an embodiment of the present disclosure may further include the step S410 of generating, by the data inference unit 140, a segmentation map for a plurality of CT images using a trained model when the CT images are input through the data collection unit 110 and the step of S420 of converting, by the data conversion unit 150, the segmentation map, generated by the data inference unit 140, into an RT-structure file and transmitting the converted RT-structure file to the radiation treatment planning system 200.

Figure 10:
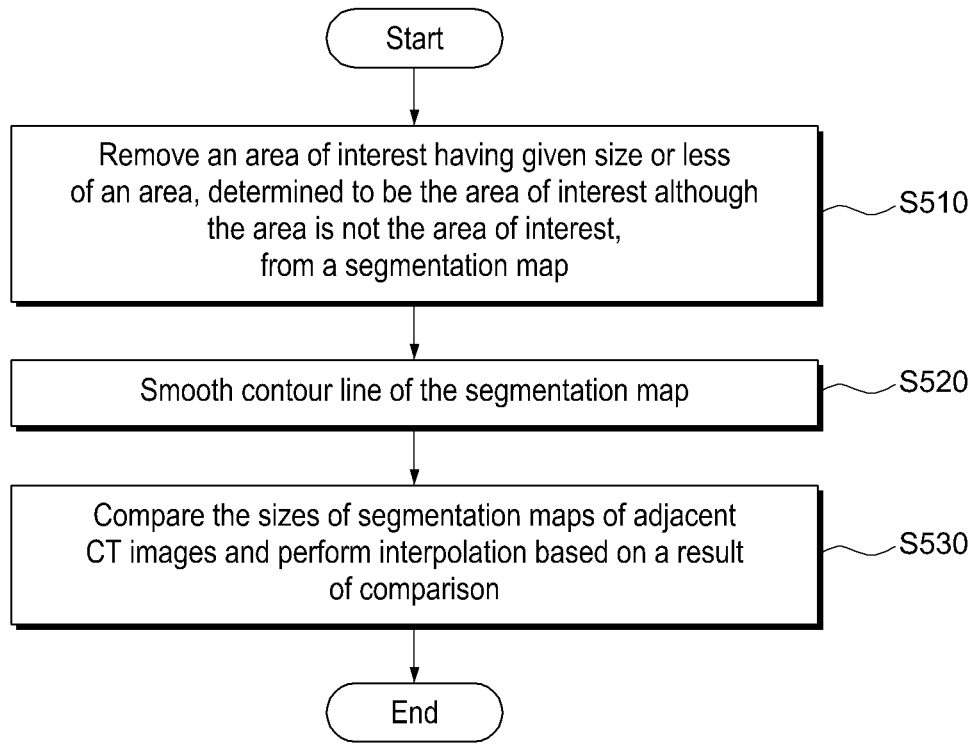
FIG. 10 is a flowchart illustrating a post-processing process for output from a trained model according to an embodiment of the present disclosure.

FIG. 10 is a flowchart illustrating a post-processing process for output from a trained model according to an embodiment of the present disclosure.

Referring to FIG. 10, the step S410 of generating a segmentation map according to an embodiment of the present disclosure may include the step S510 of removing an area of interest having a given size or less of an area, determined to be the area of interest although the area is not the area of interest, from a segmentation map, the step S520 of smoothing the contour line of the segmentation map, and the step S530 of comparing the sizes of segmentation maps of adjacent CT images and performing interpolation based on a result of the comparison.

The above-described contents of the system 100 may be applied in relation to the method according to an embodiment of the present disclosure. Accordingly, in relation to the above-described method, a description of the same contents as those of the system 100 has been omitted.

According to an embodiment of the present disclosure, there may be provided a computer-readable recording medium in which a program for executing the above-described method in a computer has been written. In other words, the above-described method may be written in the form of a computer-executable program and may be implemented in a general-purpose digital computer that drives the program using a computer-readable medium. Furthermore, the structure of data used in the above-described method may be written in a computer-readable medium through several means. The recording medium for recording an executable computer program or code for performing various methods of the present disclosure should not be understood to include temporary targets, such as carrier waves or signals. The computer-readable medium may include storage media, such as magnetic storage media (e.g., a ROM, a floppy disk and a hard disk) and optical reading media (e.g., CD-ROM and DVD).

In accordance with the system for segmenting a normal organ and/or tumor structure which is provided as an embodiment of the present disclosure, a normal organ and/or tumor portion can be automatically selected at a very high speed and a normal organ and/or tumor portion having improved accuracy can be selected, compared to a conventional system because an algorithm based on a rule arbitrarily regulated by human is not used, but an artificial intelligence model optimized for the selection of a target area for a medical image is used.

The description of the present disclosure is illustrative, and a person having ordinary knowledge in the art to which the present disclosure pertains will understand that the present disclosure may be easily modified in other detailed forms without changing the technical spirit or essential characteristic of the present disclosure. Accordingly, it should be construed that the above-described embodiments are only illustrative in all aspects, and are not limitative. For example, elements described in the singular form may be carried out in a distributed form. Likewise, elements described in a distributed form may also be carried out in a combined form.

The scope of this disclosure is defined by the appended claims rather than by the detailed description, and all changes or modifications derived from the meanings and scope of the claims and equivalents thereto should be interpreted as being included in the scope of the present disclosure.

What is claimed is:

1. A system for segmenting a normal organ and/or tumor structure based on artificial intelligence for radiation treatment planning, the system comprising:
    a data collection unit configured to
    collect a radiotherapy structure (RT-structure) file comprising a computerized tomography (CT) image of a patient and contour information of an area of interest for radiation treatment;
    a pre-processing unit configured to
    extract the contour information from the RT-structure file and generate a binary image based on the extracted contour information;
    a model training unit configured to learn parameters for generating a segmentation map indicative of the area of interest using a deep learning algorithm, based on the binary image, and generate a trained model based on the trained parameters;
    a data inference unit configured to generate a segmentation map for a plurality of CT images using the trained model when the CT images are input through the data collection unit; and
    a data conversion unit configured to convert the segmentation map, generated by the data inference unit, into an RT-structure file and transmit the converted RT-structure file to a radiation treatment planning system.

2. The system of claim 1, wherein:
    the contour information is information on locations of points forming the contour of the area of interest, and
    the pre-processing unit is configured to generate a polygonal contour line based on the information on the locations of the points and to generate the binary image by assigning a binary value based on whether the points are located inside or outside the polygonal contour line.

3. The system of claim 1, wherein the model training unit is configured to use a data augmentation algorithm in order to increase an amount of data for training.

4. The system of claim 1, wherein the model training unit is configured to:
    classify the CT images and the binary images into training data or validation data; and
    verify the plural trained models by inputting the validation data into the trained models based on the training data.

5. The system of claim 1, wherein the data inference unit is configured to:
    estimate the area of interest for the plurality of CT images at intervals of N (N is a natural number) data using the trained model; and
    perform interpolation for an estimation of an approximate value on the remaining CT images for which an area of interest has not been estimated.

6. The system of claim 1, wherein the data inference unit is configured to perform corrections on a misjudgment for an area of interest configuring the segmentation map, a size of the area of interest or a contour line of the area of interest.

7. The system of claim 6, wherein the data inference unit is configured to:
    remove an area of interest having a given size or less of an area, determined to be the area of interest although the area is not the area of interest, from the segmentation map;
    smooth a contour line of the segmentation map;
    compare sizes of segmentation maps of adjacent CT images; and
    perform interpolation based on a result of the comparison.

8. A method of segmenting a normal organ and/or tumor structure based on artificial intelligence for radiation treatment planning, the method comprising:
    collecting, by a data collection unit, a radiotherapy structure (RT-structure) file comprising a computerized tomography (CT) image of a patient and contour information of an area of interest for radiation treatment;
    extracting, by a pre-processing unit, the contour information from the RT-structure file and generating a binary image based on the extracted contour information;
    learning, by a model training unit, parameters for generating a segmentation map for a given CT image using a deep learning algorithm, based on the binary image;
    generating, by the model training unit, a trained model based on the learnt parameter;
    generating, by a data inference unit, a segmentation map for a plurality of CT images using the trained model when the CT images are input through the data collection unit; and
    converting, by a data conversion unit, the segmentation map, generated by the data inference unit, into an RT-structure file and transmitting the converted RT-structure file to a radiation treatment planning system.

9. The method of claim 8, wherein:
    the contour information extracted from the RT-structure file is information on locations of points forming the contour of the area of interest, and
    the generating of the binary image comprises generating, by the pre-processing unit, a polygonal contour line based on the information on the locations of the points and generating the binary image by assigning a binary value based on whether the points are located inside or outside the polygonal contour line.

10. The method of claim 8, wherein the generating of the trained model comprises:
  classifying the CT images and the binary images into training data or validation data; and
  verifying the plural trained models by inputting the validation data into the trained models based on the training data.

11. The method of claim 8, wherein the generating of the segmentation map comprises:
  removing an area of interest having a given size or less of an area, determined to be the area of interest although the area is not the area of interest, from the segmentation map;
  smoothing a contour line of the segmentation map; and
  comparing sizes of segmentation maps of adjacent CT images and performing interpolation based on a result of the comparison.

12. A Non-Transitory computer-readable recording medium in which a program for implementing the method of claim 8 has been written.

\* \* \* \* \*